US012310657B2

(12) United States Patent
Ikuma et al.

(10) Patent No.: US 12,310,657 B2
(45) Date of Patent: May 27, 2025

(54) EQUIPMENT FOR CRUSHING URINARY STONE

(71) Applicant: OLYMPUS CORPORATION, Tokyo (JP)

(72) Inventors: Soichi Ikuma, Akishima (JP); Eijiro Sato, Hachioji (JP); Hiroki Kazuno, Kodaira (JP)

(73) Assignee: Olympus Corporation, Tokyo (JP)

( * ) Notice: Subject to any disclaimer, the term of this patent is extended or adjusted under 35 U.S.C. 154(b) by 568 days.

(21) Appl. No.: 17/675,382

(22) Filed: Feb. 18, 2022

(65) Prior Publication Data
US 2022/0287774 A1    Sep. 15, 2022

Related U.S. Application Data

(60) Provisional application No. 63/155,337, filed on Mar. 2, 2021.

(51) Int. Cl.
| | |
|---|---|
| *A61B 1/00* | (2006.01) |
| *A61B 1/015* | (2006.01) |
| *A61B 1/018* | (2006.01) |
| *A61B 1/307* | (2006.01) |
| *A61B 18/26* | (2006.01) |
| *A61B 18/00* | (2006.01) |

(52) U.S. Cl.
CPC .............. *A61B 18/26* (2013.01); *A61B 1/015* (2013.01); *A61B 1/018* (2013.01); *A61B 1/307* (2013.01); *A61B 2018/00511* (2013.01); *A61B 2018/00982* (2013.01)

(58) Field of Classification Search
CPC ......... A61B 18/26; A61B 1/015; A61B 1/018; A61B 1/307; A61B 1/00071; A61B 1/00087; A61B 2018/00511; A61B 2018/00982; A61B 1/000137
USPC .......................................... 600/108, 129, 175
See application file for complete search history.

(56) References Cited

U.S. PATENT DOCUMENTS

| | | | |
|---|---|---|---|
| 5,630,795 A | * | 5/1997 | Kuramoto .......... A61B 1/000137 604/35 |
| 9,393,033 B2 | | 7/2016 | Zerfas et al. |

(Continued)

FOREIGN PATENT DOCUMENTS

WO    2019/176171 A1    9/2019

*Primary Examiner* — Timothy J Neal
*Assistant Examiner* — James Edward Boice
(74) *Attorney, Agent, or Firm* — Morgan, Lewis & Bockius LLP

(57) ABSTRACT

A medical endoscopic device for crushing urinary stones having an insertion portion including an optical window, an illumination window, a laser fiber, an elongate internal channel, and a procedure tube coaxially and movably disposed inside the elongate internal channel is disclosed. The distal end of the procedure tube is comprised of a distal tip portion having a diameter larger than that of the attached elongate portion. The distal tip portion of the tube also includes openings for flushing the fragments of the urinary stones and the like. The washed out fragments are suctioned through the opening between the inner diameter surface of the elongate internal channel and the outer peripheral surface of the tube and the distal tip portion may be used to scrape out the contaminated fragments of the urinary stones within the elongate internal channel.

18 Claims, 13 Drawing Sheets

(56) References Cited

U.S. PATENT DOCUMENTS

2010/0268028 A1* 10/2010 Ghabrial ............ A61B 1/00071
                                                      600/114
2018/0153376 A1*  6/2018 Begg .................. A61B 1/00091
2018/0344993 A1* 12/2018 Ganz ...................... A61B 50/30
2020/0315437 A1* 10/2020 Yuasa ................. A61B 18/1492
2020/0352650 A1* 11/2020 Chu ................... A61B 1/00137

* cited by examiner

EQUIPMENT FOR CRUSHING URINARY STONE

RELATED APPLICATION DATA

This application is based on and claims priority under 35 U.S.C. § 119 to U.S. Provisional Application No. 63/155,337, filed Mar. 2, 2021, the entire contents of which are incorporated herein by reference.

FIELD OF DISCLOSURE

The present disclosure relates generally to devices suitable for use in medical procedures and to the devices per se. In particular, embodiments of the present disclosure relate to an endoscope apparatus and endoscopic methods for crushing and collecting urinary stones from the patient's body.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

A medical practitioner generally operates medical equipment, such as endoscopes, during a medical procedure to crush and collect urinary stones from the patient's body organs, such as kidneys. The endoscope specializing in crushing and collecting urinary stones generally includes an optical window, an illumination window, a laser outlet, a water supply outlet, and a water suction outlet on its tip. The tip and following elongated tube would be inserted into the patient's body until it reaches the kidney in which the medical procedures would be performed. In order to reduce the burden on the patient's body, it is desirable that the diameter of the tip and the elongated tube of the endoscope is configured to be as small as possible. It is also desirable that the urinary stones are crushed to a certain size prior to the suction by the water suction outlet, in order to prevent the urinary stones to stuck and congest the water suction outlet or within the elongated tube.

FIG. 21 is a figure of an endoscope device disclosed in the related art (WIPO Patent Laid-open Publication No. WO 2019/176171, the entire contents of which are incorporated herein by reference). The related art endoscope device includes an insertion portion 1 consisting of endoscope insertion part 8, channel tube 12, water supply tube 13, and water suction tube 14, all of which are bundled together as a single insertion portion 1. The endoscope insertion part 8 consists of a tip portion 8a and flexible part 8b, and a distal end of the tip portion 8a includes an observation window 11a and a lighting window 11b for observing the patient's body from the inside. The channel tube 12 provides a pathway for a laser probe to penetrate and protrude from the tip opening 12a, enabling the laser probe to be positioned to direct its emitted laser onto the urinary stones and the like. The water supply tube 13 is configured to protrude at a distance d1 compared to the rest of the parts and has two water supply openings 13a and 13b. The water supply opening 13a supplies water in the same direction as the endoscope insertion part 8, channel tube 12, and water suction tube 14, and water supply opening 13b supplies water toward the water suction opening 14a of the water suction tube 14 in order to remove any contaminant that may be stuck at the opening.

FIG. 22 is a figure of another input device used in an observation device in the related art (U.S. Pat. No. 9,393,033, the entire contents of which are incorporated herein by reference) showing a distal end of the endoscope in an end view. The related art endoscope device 20 includes a tube 21 having illumination channels 22 connected to a light source 23, a visualization channel 24 for a visualization device 25, working channels 26 with associated irrigation system 27, and return channel 28 through which a suction force is created using a suction device 29. A laser fiber 30 associated with morcellating device 31 is introduced into return channel 30.

Configurations of related art endoscope devices, such as those discussed above, can be problematic. For example, the simple bundling of the endoscope insertion part 8, channel tube 12, water supply tube 13, and water suction tube 14 causes the diameter of the insertion portion 1 to be relatively large, increasing the burden on the patient. Also for example, while a return channel (such as return channel 30) may be increased in size, the overall size of the tube 20 is still a limiting factor and enlarged designs (such as return channel 30) have corners or other geometries, as well as internal features (such as laser fiber 28), that can trap contaminants and impact device performance. Overall, a more efficient design decreasing the diameter of the insertion portion while maintaining efficient irrigation and suction is desirable.

SUMMARY

Additional features and advantages will be set forth in the description that follows, and in part will be apparent from the description, or may be learned by practice of the invention. The objectives and other advantages of the disclosed input device will be realized and attained by the structure particularly pointed out in the written description and claims thereof, as well as the appended drawings.

In one aspect of the present disclosure, a medical device comprising an insertion tube and a procedure tube is disclosed. The insertion tube has an operation end and an insertion end and includes a tube wall enclosing an elongate internal channel. The procedure tube is coaxially and movably disposed inside the elongate internal channel and is comprised of an outer peripheral surface extending along a length of the procedure tube from a distal end to a proximal end, including a first portion corresponding to a first length of the outer peripheral surface at the distal end of the procedure tube, defining a distal tip portion, and a second portion corresponding to a second length of the outer peripheral surface, defining an elongate portion. In general, the first length is less than the second length, typically an order of magnitude (or more) less in length. The outer peripheral surface of the distal tip portion has a first outer diameter and the outer peripheral surface of the elongate portion has a second outer diameter, and the first outer diameter is larger than the second outer diameter.

In another aspect of the present disclosure, the outer peripheral surface includes a third portion that connects the outer peripheral surface of the distal tip portion and the outer peripheral surface of the elongate portion. The interior angle formed between the outer peripheral surface of the third portion and the outer peripheral surface of the distal tip portion has a value of greater than zero degrees and less than 180 degrees and an exterior angle formed between the outer peripheral surface of the third portion and the outer peripheral surface of the elongate portion has a value of greater than zero degrees and less than 180 degrees.

In another aspect of the present disclosure, the interior angle and the exterior angle are supplementary angles.

In another aspect of the present disclosure, the interior angle is equal to or greater than 30 degrees and the exterior angle is less than or equal to 150 degrees, or the interior angle is equal to or greater than 85 degrees and the exterior angle is less than or equal to 95 degrees.

In another aspect of the present disclosure, at least one of the interior angle and the exterior angle is 90°, or both of the interior angle and the exterior angle are 90°.

In another aspect of the present disclosure, at least one of the interior angle and the exterior angle is obtuse, or both the interior angle and the exterior angle are obtuse.

In another aspect of the present disclosure, at least one of the interior angle and the exterior angle is acute, or both the interior angle and the exterior angle are acute.

In another aspect of the present disclosure, the outer peripheral surface of the third portion is roughened, serrated, irregularly serrated, or regularly serrated.

In another aspect of the present disclosure, the distal tip portion is capable of protruding from (either partially or wholly) and retracting into the insertion end of the elongate internal channel of the insertion tube.

In another aspect of the present disclosure, the outer peripheral surface of the distal tip portion and the outer peripheral surface of the elongate portion have discontinuous diameters.

In another aspect of the present disclosure, a central axis of the procedure tube in the distal tip portion is either co-axial or non-co-axial to a central axis of the procedure tube in the elongate portion.

In another aspect of the present disclosure, at least a portion of the elongate portion is connected directly to the distal tip portion, for example, without a connecting third portion.

In another aspect of the present disclosure, the distal tip portion and the elongate portion are connected by a third portion, and each of the distal tip portion, the elongate portion, and the third portion have different diameters.

In another aspect of the present disclosure, the outer peripheral surface of the third portion extends radially outward and axially forward relative to the axis of the procedure tube, or the outer peripheral surface of the third portion extends radially outward and axially rearward relative to the axis of the procedure tube. By such an arrangement, the outer peripheral surface in the third portion can be advantageously arranged to, for example, promote ease of movement during protrusion/retraction or provide a surface to assist in removal of contaminants or, in an application related to urinary stones, assist in removal of urinary stones or pieces thereof.

In another aspect of the present disclosure, the procedure tube has an inner diameter defining a lumen, and the cross-sectional area of the lumen in the distal tip portion is larger than a cross-sectional area of the lumen in the elongate portion, and the lumen forms a chamber within the distal tip portion. A laser fiber may be positioned within the lumen of the procedure tube.

In another aspect of the present disclosure, the distal tip portion includes a flexible section capable of manipulation by an operator. The flexible section is deflectable at an angle relative to a central axis of the distal tip portion.

In another aspect of the present disclosure, the laser fiber extendible along a lumen of the procedure tube is affixed to the distal tip portion of the procedure tube.

In another aspect of the present disclosure, the distal tip portion includes an opening or more than one opening in a wall of the procedure tube, and the opening(s) extend from the outer peripheral surface to the lumen. Further, the opening provides a portion of a flow path from a supply of a fluid to the outer peripheral surface of the distal tip portion.

In another aspect of the present disclosure, the opening is a slit.

In another aspect of the present disclosure, the outer peripheral surface of the distal tip portion includes a measuring scale.

In another aspect of the present disclosure, the outer peripheral surface of the proximal end of the tube includes a measuring scale and a water-tightening valve.

In another aspect of the present disclosure, the procedure tube that is coaxially and movably inserted into an elongated internal channel for use is disclosed. The procedure tube is comprised of an inner peripheral surface extending along a length of the procedure tube from a distal end to a proximal end, wherein the inner peripheral surface includes two portions, a first portion corresponding to a first length of the inner peripheral surface at the distal end of the procedure tube and defining a distal tip portion and a second portion corresponding to a second length of the inner peripheral surface and defining an elongate portion. Further, the inner peripheral surface of the distal tip portion has a first inner diameter and the inner peripheral surface of the elongate portion has a second inner diameter, and the second inner diameter is larger than the first inner diameter.

In another aspect of the present disclosure, the inner peripheral surface of the procedure tube includes a third portion, the third portion connects the inner peripheral surface of the distal tip portion and the inner peripheral surface of the elongate portion. The interior angle formed between the inner peripheral surface of the third portion and the inner peripheral surface of the distal tip portion has a value of greater than 90 degrees and less than 180 degrees and an exterior angle formed between the inner peripheral surface of the third portion and the inner peripheral surface of the elongate portion has a value of greater than 90 degrees and less than 180 degrees.

In another aspect of the present disclosure, the procedure tube includes a laser fiber extendible along a lumen of the procedure tube.

In another aspect of the present disclosure, the distal tip portion or the third portion of the procedure tube includes an opening in a wall of the procedure tube that extends from the outer peripheral surface to the lumen.

In another aspect of the present disclosure, the opening of the procedure tube provides a portion of a flow path from a supply of a fluid to the outer peripheral surface of the distal tip portion or the third portion.

In another aspect of the present disclosure, the distal tip portion or the third portion of the procedure tube includes more than one openings.

In another aspect of the present disclosure, the opening of the procedure tube is a slit.

In another aspect of the present disclosure, the flow path of the procedure tube is configured to supply fluid towards the distal end of the procedure tube.

In another aspect of the present disclosure, the central axis of the opening is oblique relative to the longitudinal axial of the procedure tube.

In another aspect of the present disclosure, the central axis of the opening is oblique towards the distal end of the procedure tube.

In another aspect of the present disclosure, the opening area in a wall of the procedure tube is larger than the opening area of the distal end of procedure tube.

In another aspect of the present disclosure, the procedure tube includes a laser fiber extendible along a lumen of the procedure tube, and the opening area in a wall of the procedure tube is larger than the opening area between the distal end of procedure tube and laser fiber.

In another aspect of the present disclosure, the outer peripheral surface of the near distal end of the procedure tube includes a different colored portion circumventing the procedure tube.

In another aspect of the present disclosure, the outer peripheral surface of the distal end of the procedure tube includes a measuring scale.

In another aspect of the present disclosure, the outer peripheral surface of the proximal end of the procedure tube includes a measuring scale.

In another aspect of the present disclosure, the outer peripheral surface of the proximal end of the procedure tube includes a water-tightening valve.

In another aspect of the present disclosure, an endoscope comprised of an insertion tube having an optical window, an illumination window, an elongate internal channel extending from an operation end to an insertion end, a procedure tube coaxially and movably disposed inside the elongate internal channel, and a laser fiber coaxially and movably disposed inside an inner lumen of the procedure tube is disclosed. The procedure tube is further comprised of an outer peripheral surface extending along a length of the procedure tube from a distal end to a proximal end, and the outer peripheral surface includes two portions, a first portion corresponding to a first length of the outer peripheral surface at the distal end of the procedure tube and defining a distal tip portion, and a second portion corresponding to a second length of the outer peripheral surface and defining an elongate portion. The outer peripheral surface of the distal tip portion has a first outer diameter and the outer peripheral surface of the elongate portion has a second outer diameter, and the first outer diameter is larger than the second outer diameter.

In another aspect of the present disclosure, an endoscope comprised of an insertion tube having an optical window, an illumination window, and an elongate internal channel extending from an operation end to an insertion end is disclosed. The elongate internal channel includes three portions, a first portion corresponding to a first length of the elongate internal channel and defining a distal tip portion, a second portion corresponding to a second length of the elongate internal channel and defining an elongate portion, and the third portion connects the elongate internal channel of the distal tip portion and the elongate internal channel of the elongate portion. The elongate internal channel of the distal tip portion has a first inner diameter and the elongate internal channel of the elongate portion has a second inner diameter and the second inner diameter is larger than the first inner diameter. The exterior angle formed between the elongate internal channel of the third portion and the elongate internal channel of the distal tip portion has a value of greater than 150 degrees and an interior angle formed between the inner peripheral surface of the third portion and the inner peripheral surface of the elongate portion has a value of greater than 150 degrees.

In another aspect of the present disclosure, the length of the elongate internal channel of the distal tip portion is shorter than the first inner diameter.

In another aspect of the present disclosure, the procedure tube is coaxially and movably disposed inside the elongate internal channel and the length of the elongate internal channel of the distal tip portion is shorter than the difference between the first inner diameter and the outer diameter of the procedure tube.

In another aspect of the present disclosure, a method for crushing an urinary stone includes passing a procedure tube through an elongate internal channel of an insertion tube of an endoscope, placing the procedure tube through the elongate internal channel at a position protruding from an insertion end of the elongate internal channel, placing a laser fiber through an inner lumen of the procedure tube at a position protruding from a distal end portion of the procedure tube, flushing fluid through the inner lumen of the procedure tube and out from an opening configured at the distal end portion of the procedure tube, fragmenting an object by irradiating the object using laser energy passing through the laser fiber, and using a size of an opening between an inner diameter surface of the elongate internal channel and an outer peripheral surface of the procedure tube to selectively suction and pass fragments of the object having a first size while preventing from passing fragments of the object of a second size, the second size being larger than the first size.

In another aspect of the present disclosure, a method for crushing an urinary stone further includes moving the distal end portion of the procedure tube to protrude from the insertion end of the elongate internal channel to enlarge the size of the opening between the inner diameter surface of the elongate internal channel and the outer peripheral surface of the procedure tube, and retracting the distal end portion of the procedure tube back into the elongate internal channel.

In another aspect of the present disclosure, a method for crushing an urinary stone further includes moving the distal end portion of the procedure tube within the elongate internal channel to have the outer peripheral surface of the procedure tube contact and scrape out toward the operation end of the elongate internal channel any fragments of the object present in the elongate internal channel.

The term "patient," as used herein, comprises any and all organisms and includes the term "subject." A patient can be a human or an animal.

Other systems, methods, features and advantages will be, or will become, apparent to one with skill in the art upon examination of the following figures and detailed description. It is intended that all such additional systems, methods, features and advantages be included within this description, be within the scope of the present disclosure, and be protected by the following claims. Nothing in this section should be taken as a limitation on those claims. Further aspects and advantages are discussed below in conjunction with the embodiments of the disclosed input device. It is to be understood that both the foregoing general description and the following detailed description of the disclosed input device are examples and explanatory and are intended to provide further explanation of the disclosed input device as claimed.

BRIEF DESCRIPTION OF THE DRAWINGS

The following detailed description of preferred embodiments can be read in connection with the accompanying drawings in which like numerals designate like elements and in which.

Figure 1A:
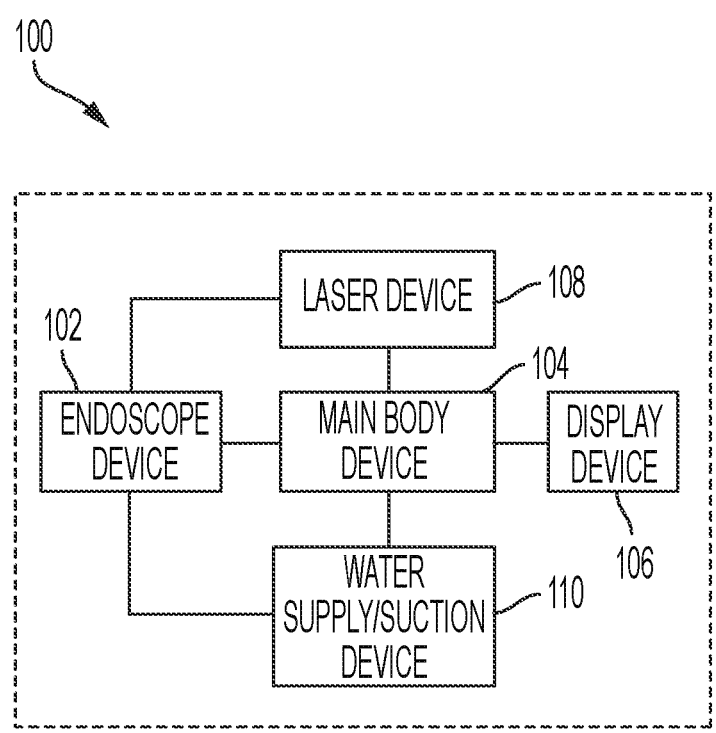
FIG. 1A is a block diagram illustrating a configuration of an endoscope system that includes an endoscope device according to an embodiment of the present disclosure.

Throughout all of the drawings, dimensions of respective constituent elements are appropriately adjusted for clarity. For ease of viewing, in some instances only some of the named features in the figures are labeled with reference numerals.

DETAILED DESCRIPTION

FIG. 1A is a block diagram of an endoscope system according to an embodiment of the present invention. The endoscope system 100 is configured to include an endoscope device 102, a main body device 104, a display device 106, a laser device 108, and a water supply/suction device 110.

The endoscope system 100 is used for observing inside a patient and crushing urinary stones and the like existing within the patient and collecting them through water supply and suction. The endoscope device 102 collects images from within the patient, allowing the operator to observe and perform various medical procedures while viewing the endoscopic image displayed on the display device 106.

The main body device 104 includes an image processor having a drive circuit for driving the image sensor and an image processing circuit for receiving images from the image sensor and generating an image signal. Furthermore, the main body device 104 has a built-in light source or power source for illumination light. The illumination light from the light source passes through the light guide and is emitted from the illumination window within the endoscope device 102. The display device 106 receives the image signal from the main body device 104 and displays an endoscopic image on the display device 106.

The laser device 108 generates laser beams for crushing urinary stones and the like. The generated laser beams pass through the main body device 104 to the endoscope device 102 and is emitted from the laser fiber placed at the tip of the endoscope device 102 to make the crush. The operator may apply lasers to urinary stones or the like while looking at the endoscopic image captured by the endoscope device 102 and displayed on the display device 106.

The water supply/suction device 110 supplies fluids such as physiological saline and suctions the fluids from inside the patient. Therefore, the water supply/suction device 110 includes a water supply pump and a water suction pump. The fluids are supplied from the water supply pump and suctioned by the water suction pump via a procedure tube to be discussed later.

New fluids will be constantly supplied into the patient by the water supply/suction device 106 and constantly suctioned out by the water supply/suction device 106. Therefore, the operator may crush and collect the fragments of the urinary stones and the like by observing the endoscopic image of the patient while the fluids are being constantly supplied and suctioned out from the patient.

Figure 1B:
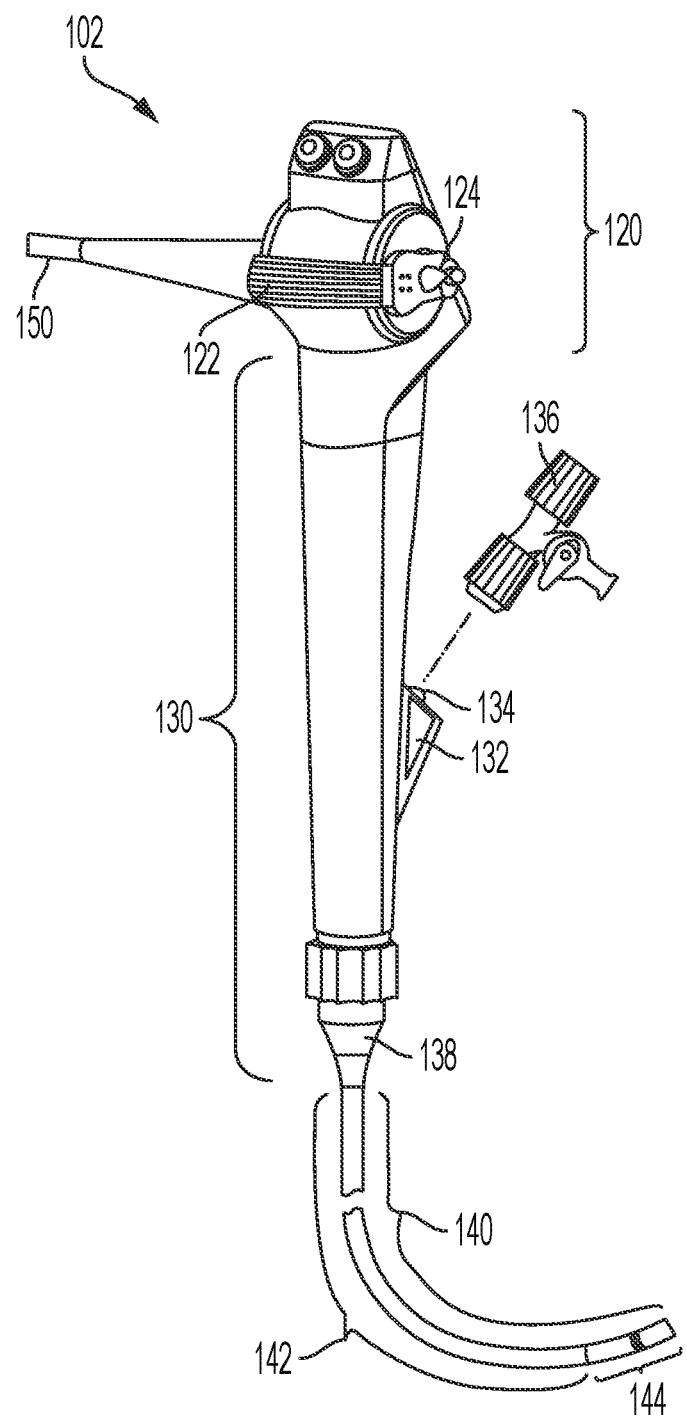
FIG. 1B is a schematic illustration of an example endoscope device.

FIG. 1B is a schematic illustration of an example endoscope device 102. The example endoscope device 102 includes a control section 120 which contains control wheels 122 and manipulation controls 124. Below the control section 120 is the grip section 130 which houses a biopsy/accessory port 132 and boot section 138. The biopsy/accessory port 132 for inserting various equipment into the patient includes a connecting port 134 for connecting to accessories such as water valve 136, which serves to connect the said various equipment to the water supply/suction device 110. The boot section 138 leads to the insertion tube 140, which has an operation end 142 (positioned toward the control section 132) and an insertion end 144 (which is the free end that is inserted into a patient's body). Also connected to the control section 132 is an umbilical cord 150, which connect to the main body device 104.

Figure 2:
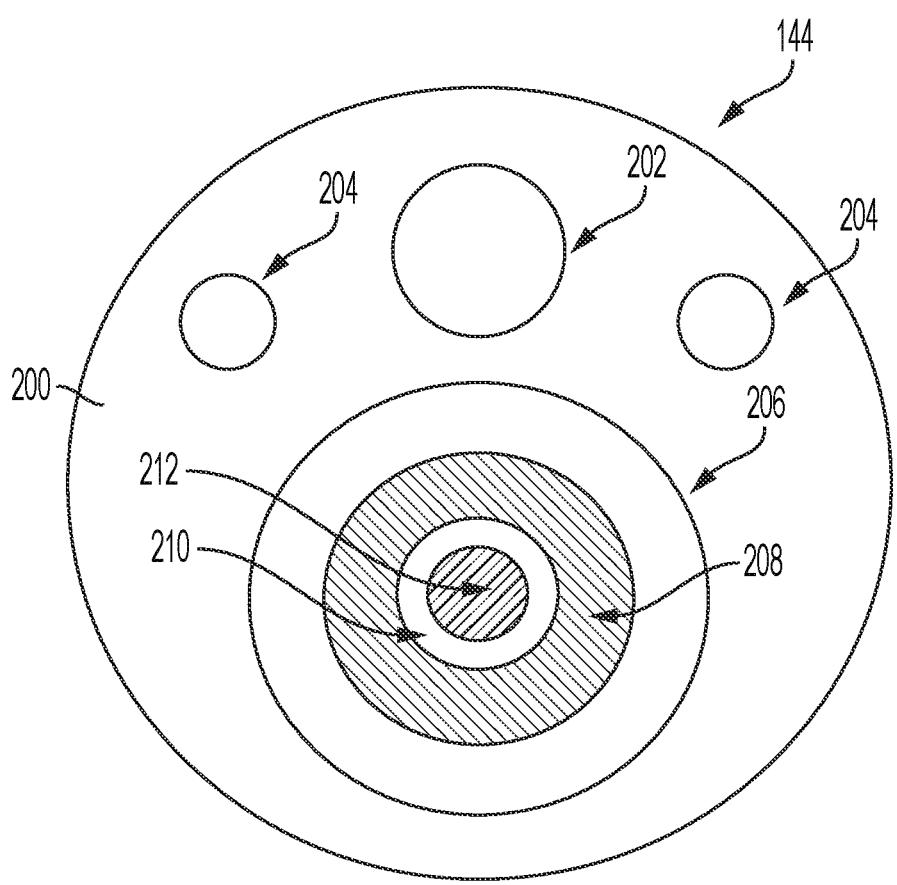
FIG. 2 schematically illustrates, in an end view, a distal portion of an embodiment of the disclosed endoscope device.

FIG. 2 is a diagram showing the end view of an insertion end 144 of the insertion tube 140 of the endoscope device 130, which would be inserted into a patient. The end view in FIG. 2 shows the end face surface 200 of the insertion end 144 and in which several features are shown, including: an observation window 202, two illumination windows 204, an opening of the elongate internal channel 206, a procedure tube 208, an opening of the water supply channel 210, and a laser fiber 212. In the illustrated embodiment, at least end surfaces of each of the procedure tube 208, the opening of the water supply channel 210, and the laser fiber 212 are arranged concentrically within the elongate internal channel 206, preferably concentrically with a central axis of the elongate internal channel 206.

The observation window 202 allows the operator to observe within the patient's body where the medical procedure is performed. An objective optical system such as optical lens is arranged at the tip of the insertion end 144 of the endoscope insertion tube 140, constituting the observation window 202. At the rear side of the observation window 202, an elongated image guide of the optical fiber bundle is arranged. The elongated image guide supplies the images to the image sensor and the image processing circuit associated with the main body device 104.

In another embodiment, an image pickup device, such as a CMOS image sensor, may be placed at the observation window 202. In that case, the signal line extending from the image sensor is placed through the endoscope device 102 and connected to the main body device 104, where the transferred image signal of the image sensor would be processed by the image processing circuit.

The one or more illumination windows 204 allow the observation window 202 to capture images within the patient's body, which would otherwise lack sufficient lighting. An illumination optical system such as an optical lens is provided at the insertion end 144 of the insertion tube 140, constituting the illumination window 204. At the rear side of the illumination windows 204, an elongated light guide of the optical fiber bundle is arranged. The base end of the light guide is connected to the light source in the main body device 104, which transmits the illumination light to be emitted from the illumination windows 204.

In another embodiment, a light emitting element, such as a light emitting diode (LED), may be provided at the illumination windows 204. In that case, the power supply line extending from the light emitting element is connected to the power source placed at the main body device 104.

The body of the insertion tube 140 forms or includes a tube wall that encloses the elongate internal channel 206. The elongate internal channel 206 extends from an insertion end 144 of the insertion tube 140 to an operation end 142 of the insertion tube 140. The procedure tube 208 may be coaxially and movably disposed in the elongate internal channel 206. From the insertion end 144, an operator may supply water using the procedure tube 208 or suction the crushed urinary stones and the like. From the operation end 142, an operator may collect the suctioned objects or insert procedural equipment, such as procedure tube 208, laser fiber 212, or other medical equipment. A water tightening valve at the operation end 142 of the elongate internal channel 206, e.g., using the biopsy/accessory port 136, can prevent the suctioned water from coming out, but at the same time allowing medical equipment such as procedure tube 208 to be inserted within the elongate internal channel 206.

The laser device 108 produces laser beams suitable for crushing urinary stones and the like. The laser fiber 212, constituting a portion of a surgical laser treatment device, extends from the laser device 108, and is configured to be insertable into the procedure tube 208 included in the endoscope device 102 and extend to the distal end thereof. The procedure tube 208 has an inner lumen constituting the water supply channel 210 and through which the laser fiber 212 can be inserted (enabling insertion of the laser fiber 212 to the location of treatment within the patient's body). The operator may insert the laser fiber 212 into the procedure tube 208 and emit laser light from the tip of the laser fiber 212 at the location of treatment. The laser fiber 212 may protrude from the opening of the water supply channel 210 of the procedure tube 208 and the emitted laser beam crushes the urinary stones and the like within the patient's body. Note that the laser fiber 212 is used here for crushing urinary stones and the like, but alternative treatment devices can be similarly used, such as an electric scalpel device and the like used for excising tumors and the like through the water supply channel 212.

Figure 3:
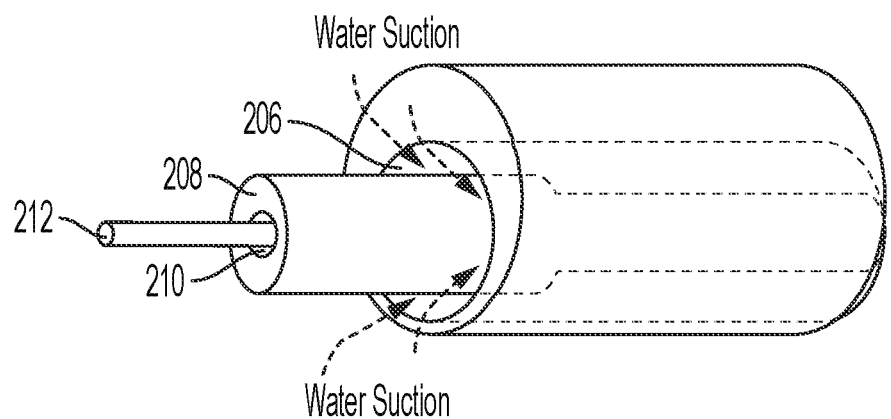
FIG. 3 schematically illustrates, in a perspective view, a distal portion of an embodiment of the disclosed endoscope device and illustrating the irrigation flow path when the features are in the illustrated positions.

FIG. 3 is a diagram of the insertion end 144 of the insertion tube 140 of a medical device and showing the opening of the elongate internal channel 206, procedure tube 208, an opening of the water supply channel 210, and laser fiber 212. In FIG. 3, the procedure tube 208 and laser fiber 212 are each shown in a partial extended position (also called protrusion position). Fluids, such as physiological saline solution, may be supplied from the opening of the water supply channel 210 and suctioned through the opening between the inner peripheral surface of the elongate internal channel 206 and the outer peripheral surface of the procedure tube 208 using the water suction pump within the water supply/suction device 110. The urinary stones or the like crushed by the laser beam emitted from laser fiber 212 may be selectively suctioned through the said opening and passed through the elongate internal channel 206 to be collected at the other end of the elongate internal channel 206, typically at or towards the operation end 142 of the insertion tube 140.

Further, on the inner peripheral surface of the elongate internal channel 206, a spiral groove may be formed along the longitudinal axis direction of the elongate internal channel 206. Such a groove causes the suctioned physiological saline to flow spirally in the elongate internal channel 206, so as to generate a directed flow or vortex. The pressure of the directed flow vortex is lower near the central axis of the elongate internal channel 206 and higher near the inner peripheral surface of the elongate internal channel 206. As a result of the different pressures, the crushed stone pieces will flow more easily near the central axis of the inner peripheral surface of the elongate internal channel 206, so that the crushed stone fragments (or other contaminates) are less likely to be clogged in or adhere to the inner peripheral surface of the elongate internal channel 206.

Figure 4:
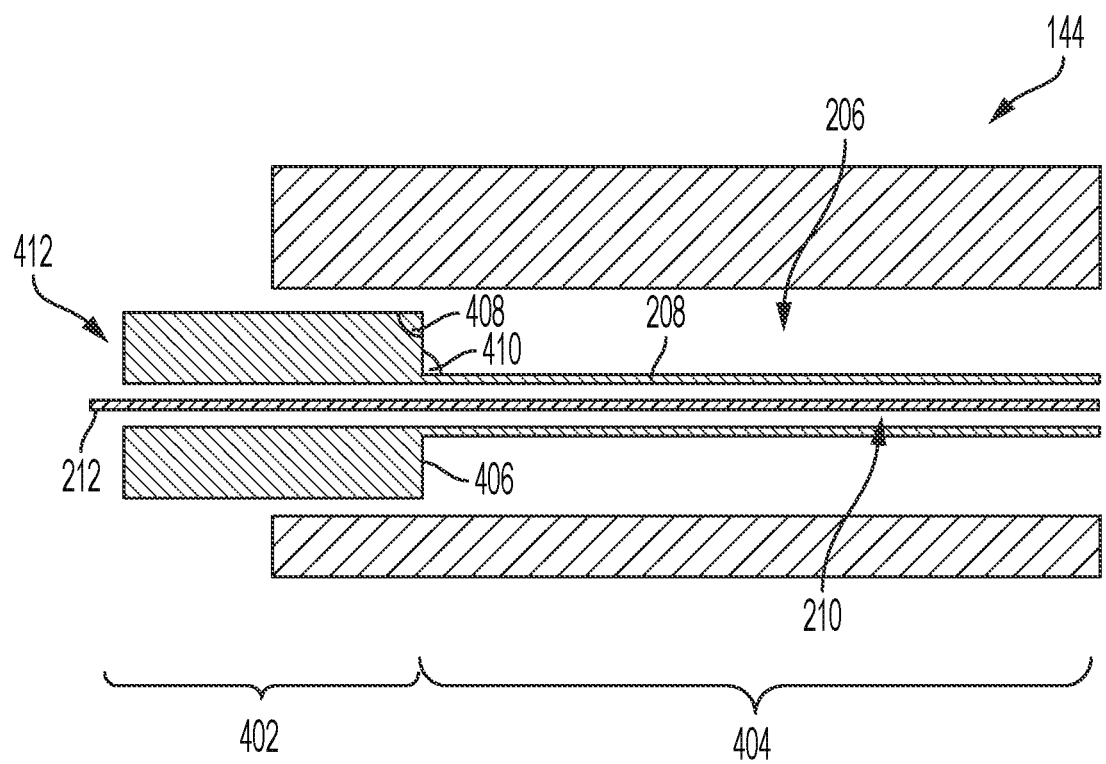
FIG. 4 schematically illustrates, in a side, cross-sectional view, a distal portion of an embodiment of the disclosed endoscope device with an embodiment of a distal tip portion.

FIG. 4 is a diagram of the insertion end 144 of the insertion tube 140 showing, in cut-away view, the inner lumen of the elongate internal channel 206, procedure tube 208, water supply channel 210, and laser fiber 212. The procedure tube 208 is coaxially and movably disposed inside the elongate internal channel 206 and the outer peripheral surface of the procedure tube 208 extends along the length of the procedure tube 208, from a distal end 412 to a proximal end (not shown), which generally correspond with the insertion end 144 and the operation end 142 of the insertion tube 140, respectively. The outer peripheral surface of the procedure tube 208 includes two portions, a distal end portion 402 and elongate portion 404. The outer peripheral surface of the distal end portion 402 and the elongate portion 404 are connected with a connecting portion 406. As described in FIG. 4, the outer diameter of the distal end portion 402 is larger than the outer diameter of elongate portion 404.

The connecting portion 406 connects the outer peripheral surface of the distal tip portion 402 and the outer peripheral surface of the elongate portion 404. An interior angle 408 is formed between the outer peripheral surface of the connecting portion 406 and the outer peripheral surface of the distal tip portion 402 (as illustrated in FIG. 4). An exterior angle 410 is formed between the outer peripheral surface of the connecting portion and the outer peripheral surface of the elongate portion 404 (as illustrated in FIG. 4). Both the interior angle 408 and the exterior angle 410 have a value of greater than zero degrees and less than 180 degrees and the angles of interior angle 408 and exterior angle 410 may be supplementary. FIG. 4 discloses both the interior angle 408 and the exterior angle 410 being 90 degrees.

Figure 5:
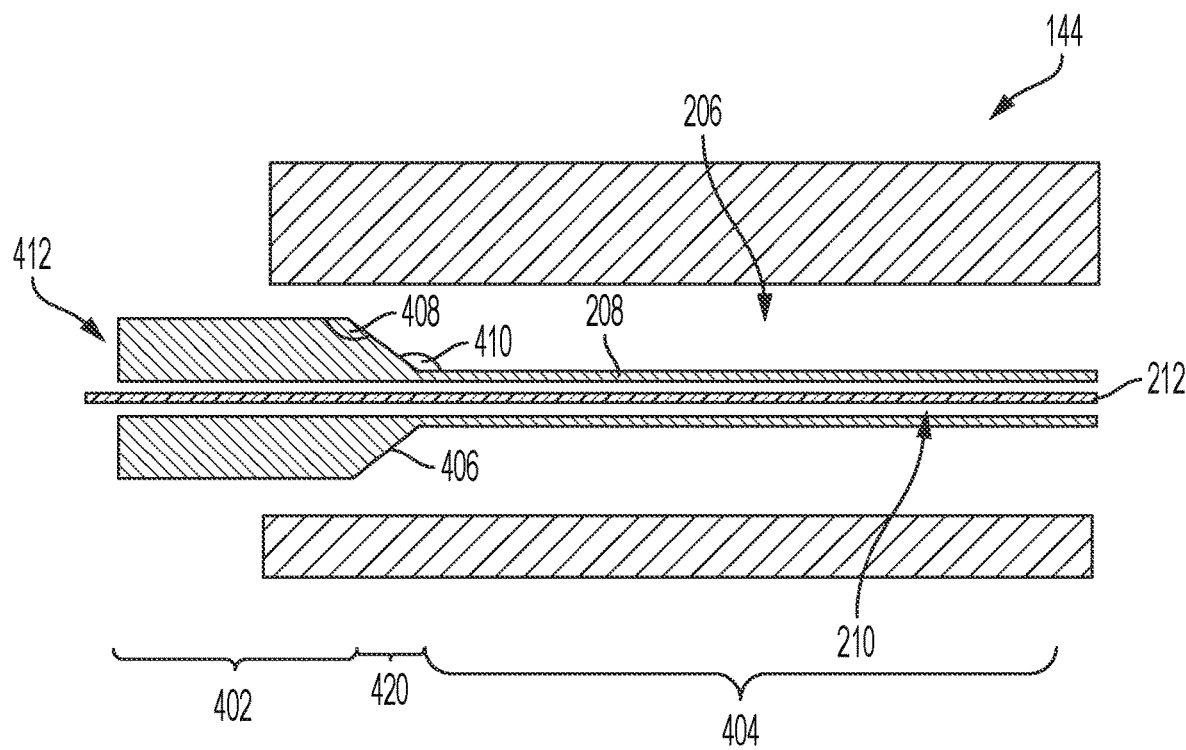
FIG. 5 schematically illustrates, in a side, cross-sectional view, a distal portion of an embodiment of the disclosed endoscope device with another embodiment of a distal tip portion.
Figure 6:
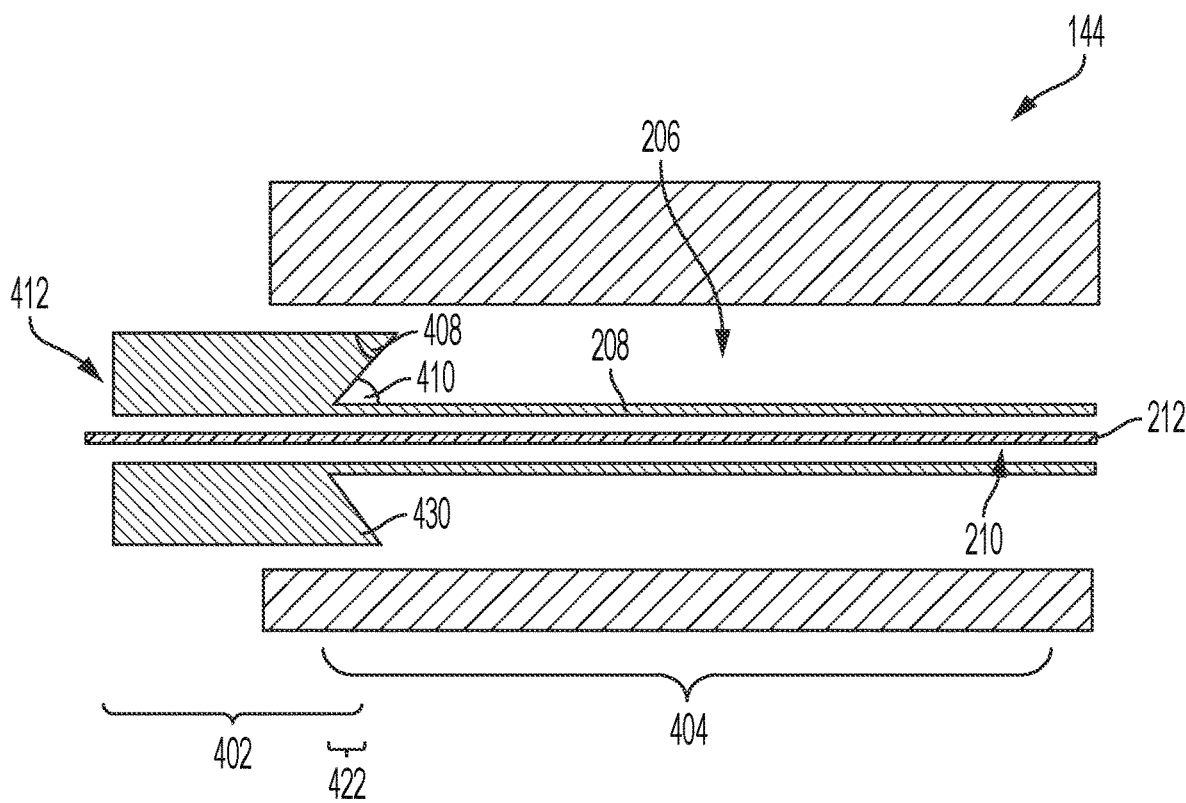
FIG. 6 schematically illustrates, in a side, cross-sectional view, a distal portion of an embodiment of the disclosed endoscope device with another embodiment of a distal tip portion.

FIG. 5 is a diagram of the insertion end 144 of the insertion tube 140 showing another variation of the distal tip portion 402, with both the interior angle 408 and exterior angle 401 being an obtuse angle. FIG. 6 discloses another variation of the distal tip portion 402, with both the interior angle 408 and exterior angle 410 being an acute angle. Although FIGS. 5 and 6 illustrate embodiments in which each of the interior angle 408 and exterior angle 401 are of the same angle type, i.e., either both obtuse or both acute, it is expressly contemplated that a first one of the interior angle 408 and exterior angle 401 can be acute and a second one of the interior angle 408 and exterior angle 401 can be obtuse, in which case, the connecting portion 406 has a complex shape, such as comprising one or more of a curved section, or multiple planar sections joined together to extend, in combination, from a first end of the connecting portion 406 that connects to the outer peripheral surface of the distal tip portion 402 to a second end of the connecting portion 406 that connects to the outer peripheral surface of the elongate portion 404.

Also and as shown in FIGS. 5 and 6, in some embodiments (such as illustrated in FIG. 5), the outer peripheral surface of the elongate portion 404 is axially separated from the distal tip portion 402 (see portion 420), while in other embodiments (such as illustrated in FIG. 6), the outer peripheral surface of the elongate portion 404 axially overlaps the distal tip portion 402 (see portion 422). In still other embodiments (such as illustrated in FIG. 4), the outer peripheral surface of the elongate portion 404 axially abuts the distal tip portion 402.

As shown in FIG. 3, fragments of the urinary stones and the like having a size smaller than the space between the inner peripheral surface of the elongate internal channel 206 and the outer peripheral surface of the procedure tube 208 may be suctioned using the water suction pump within the water supply/suction device 110. In general, the fragments of the urinary stones would not be sphere shaped and would be a cuboid with a long axis and a short axis. If the short axis of the fragments is smaller than the opening between the inner diameter of the elongate internal channel 206 and the outer diameter of the distal tip portion 402, the fragments will be sucked into the elongate internal channel 206. However, when the fragments flow into the elongate internal channel 206, the plane of large projected area will become perpendicular to the flow due to the laws of physics. At that time, if the long axis is larger than the space between the inner diameter of the elongate internal channel 206 and the outer diameter of the elongate portion 404, the fragments may get stuck within the said space. Therefore, it is advisable to set the opening between the inner diameter of the elongate internal channel 206 and the outer diameter of the distal tip portion 402 and the space between the inner diameter of the elongate internal channel 206 and the outer peripheral surface of the elongate portion 404 according to the ratio (aspect ratio) of the long axis and the short axis of the fragments to be collected. Specifically, it is advisable to optimally design the outer diameter of the distal tip portion 402 and the outer diameter of the elongate portion 404. The operator may move the procedure tube 208 and make the distal tip portion 402 to protrude from the elongate internal channel 206 at the insertion end 144. The operator may further move the procedure tube 208 and make the distal tip portion 402 completely protrude outside the elongate internal channel 206 and also at least a portion of the elongate portion 404 to protrude outside the elongate internal channel 206. In such a position, due to the dissimilar size of the distal tip portion 402 and the elongate portion 404, the size of the space between the inner peripheral surface of the elongate internal channel 206 and the outer peripheral surface of the procedure tube 208 increases (as compared to the position where a portion of the distal tip portion 402 remains within the elongate internal channel 206). Note that in case of the shape variation of the distal tip portion 402 shown in FIG. 5, where both the interior angle 408 and exterior angle 410 being an obtuse angle, an operator need not move the procedure tube 208 to the same extent as with the shape variation of the distal tip portion 402 shown in FIG. 4 to reveal the elongate portion 404 in order to increase the space for the fragments to pass through. Rather, with the shape variation of the distal tip portion 402 shown in FIG. 5, the space between the inner peripheral surface of the elongate internal channel 206 and the outer peripheral surface of the procedure tube 208 will gradually increase because of the slope of the connecting portion 406.

After suctioned fragments passes through the outer peripheral surface of the distal tip portion 402 of the procedure tube 208, the fragments would travel along the inner peripheral surface of the elongate internal channel 206 and the outer peripheral surface of the elongate portion 404, and exit the elongate internal channel 206, e.g., from the operation end 142 of the elongated channel 206.

In case the suctioned fragments are stuck between the inner peripheral surface of the elongate internal channel 206 and the outer peripheral surface of the elongate portion 404 of the procedure tube 208, an operator may move the procedure tube 208 back and forth inside the elongate internal channel 206. As a result, the stuck fragment will be removed from its stuck position, forcing the short axis of the fragment to face the radial direction of the elongate internal channel 206. If the problem still persists, an operator may retract the procedure tube 208 back into the elongate internal channel 206. The distal end portion 402 of the procedure tube 208 may be moved within the elongate internal channel 206 to have the outer peripheral surface of the procedure tube 208, especially the outer peripheral surface of the connecting portion 406, contact and scrape out the stuck fragments toward the operation end of the elongate internal channel 206.

In order to improve the contacting and scraping function of the procedure tube 208 and the connecting portion 406, the outer peripheral surface of the connecting portion 406 may include surface features, such as being roughened, serrated, irregularly serrated, or regularly serrated. In another variation, the connecting portion 406 can be angled, such as shown in FIG. 6, to be oriented so as to bias any material contacted at an outer end region 430 of the connecting portion 406 to move toward the apex of the exterior angle 410 when the procedure tube 208 is moved in the retraction direction. Such surface features and angled connecting portions 406 can be used individually or combined.

Figure 7:
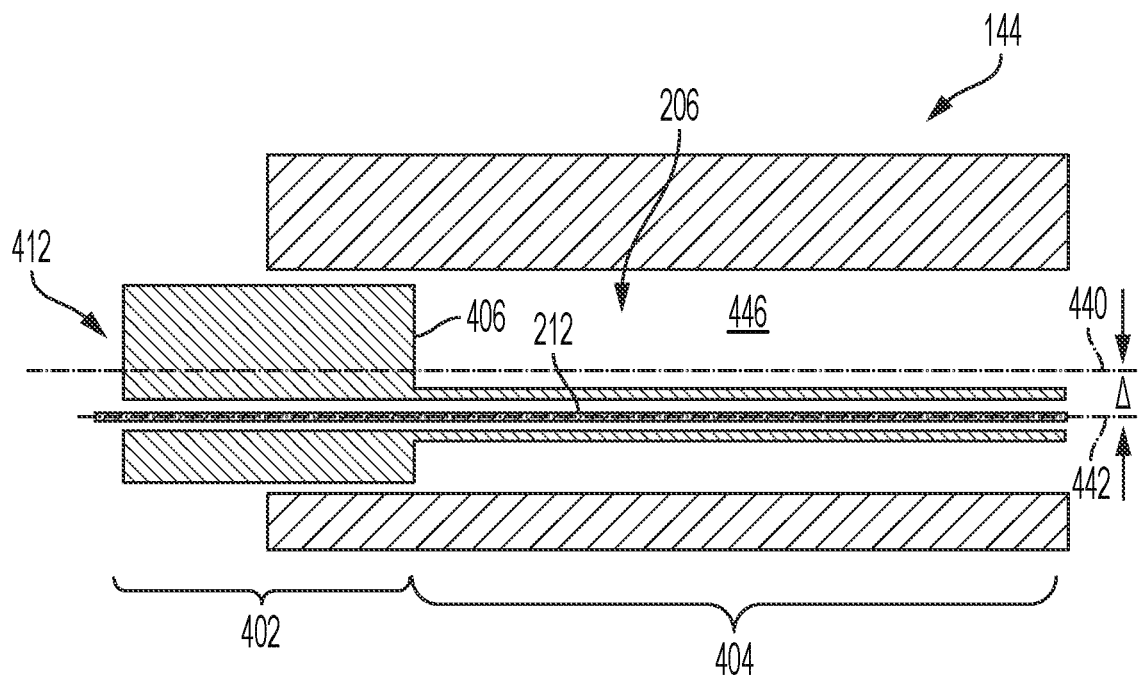
FIG. 7 schematically illustrates, in a side, cross-sectional view, a distal portion of an embodiment of the disclosed endoscope device with another embodiment of a distal tip portion.

FIG. 7 is a diagram of the insertion end 144 of the insertion tube 140 showing another variation of the distal tip portion 402, in which a central axis 440 of the procedure tube 208 in the distal tip portion 402 is non-co-axial to the central axis 442 of the procedure tube 208 in the elongate portion 404. This non-co-axial relationship results in a separation distance (Δ) between central axis 440 and central axis 442 and this configuration (in combination with the dissimilar thickness or diameters of the distal tip portion 402 and the elongate portion 404 relative to their respective central axis) creates an unbalance in the space 446 between the inner peripheral surface of the elongate internal channel 206 and the outer peripheral surface of the elongate portion 404, and this larger space 446 may allow larger fragments to go through the elongate internal channel 206.

Figure 8:
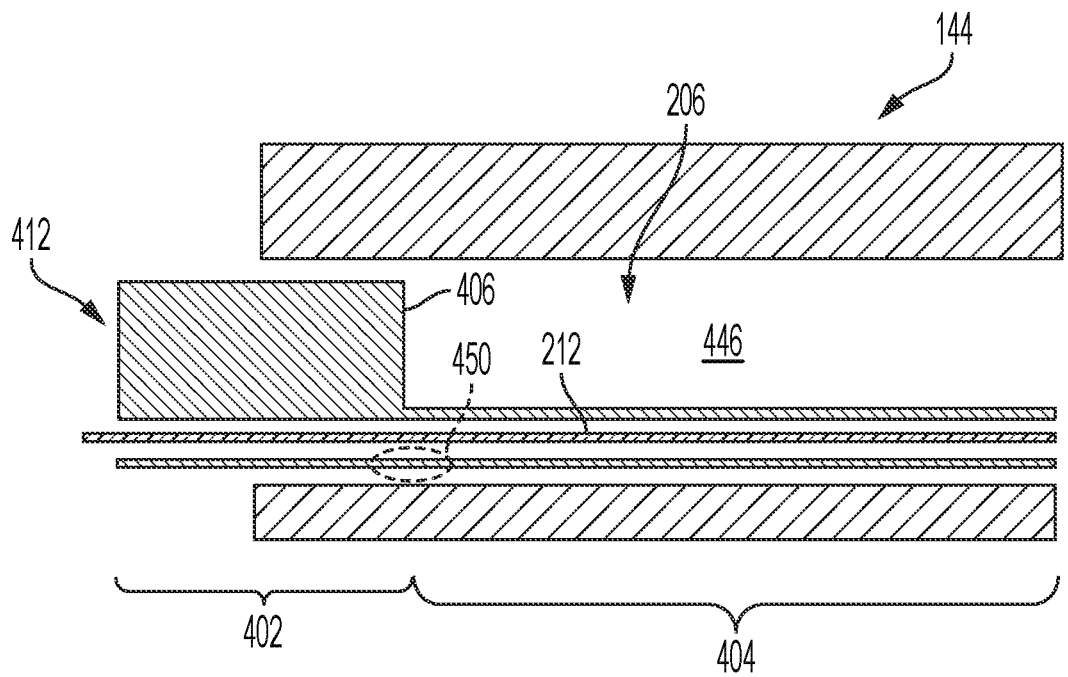
FIG. 8 schematically illustrates, in a side, cross-sectional view, a distal portion of an embodiment of the disclosed endoscope device with another embodiment of a distal tip portion.

FIG. 8 is a diagram of the insertion end 144 showing another variation of the distal tip portion 402, in which a region 450 of the elongate portion 404 is connected directly to the distal tip portion 402 without the connecting portion 406. This configuration creates further unbalance in the space 446 between the inner peripheral surface of the elongate internal channel 206 and the outer peripheral surface of the elongate portion 404, and this larger space 446 may allow even larger fragments to go through the elongate internal channel 206.

Figure 9:
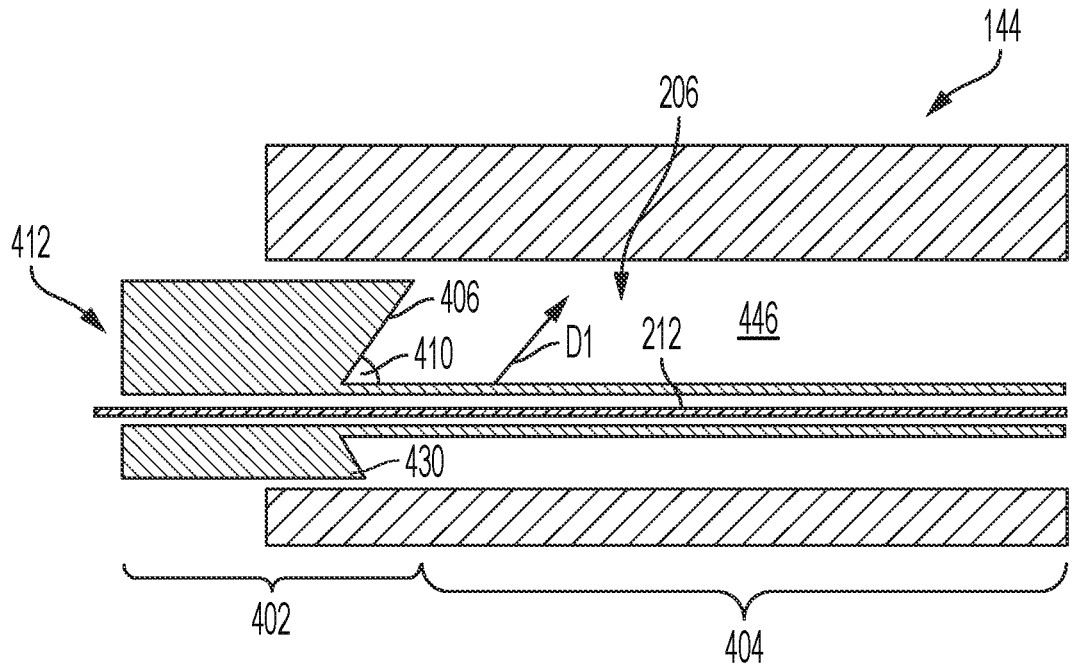
FIG. 9 schematically illustrates, in a side, cross-sectional view, a distal portion of an embodiment of the disclosed endoscope device with another embodiment of a distal tip portion.

FIG. 9 is a diagram of the insertion end 144 showing variations of the distal tip portion 402, in which, similar to FIG. 7, unbalance exists in the space 446 between the inner peripheral surface of the elongate internal channel 206, and the outer peripheral surface of the connecting portion 406 extends radially outward and axially rearward relative to the axis of the procedure tube 208, rearward viewed from the distal end 412 of the procedure tube 208 (for illustration purposes, this direction is shown by arrow D1). This configuration allows larger fragments of the urinary stones and the like to go through the elongate internal channel 206 due to the unbalance in space 446, as well as increasing the bias for any fragments contacted at an outer end region 430 of the connecting portion 406 to move toward the apex of the exterior angle 410 when the procedure tube 208 is moved in the retraction direction.

Figure 10:
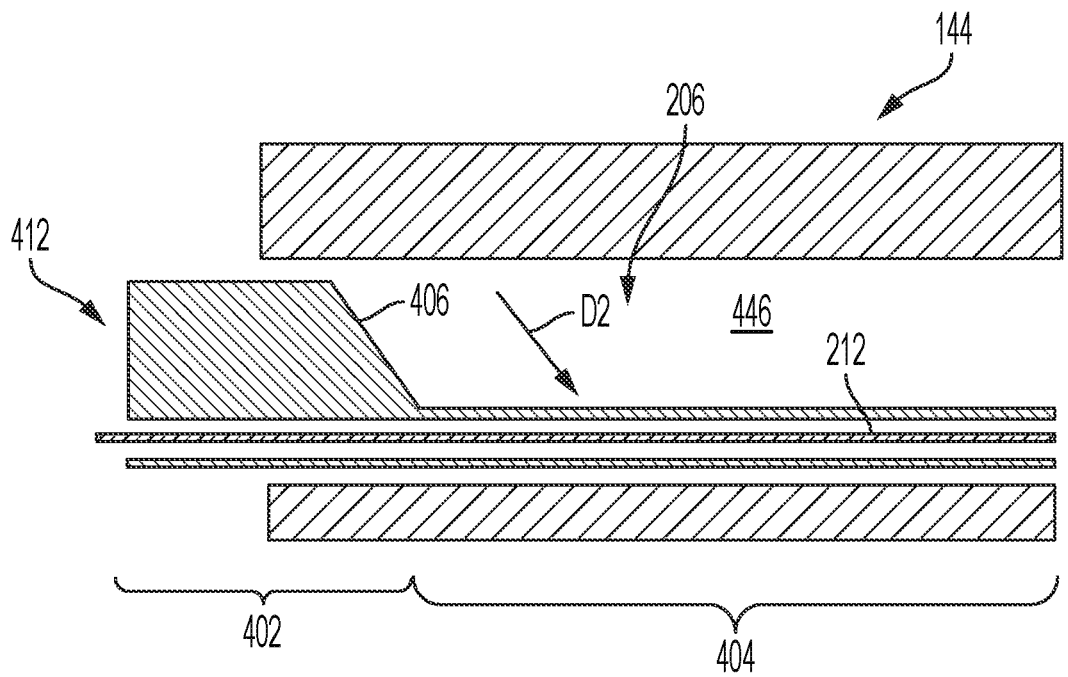
FIG. 10 schematically illustrates, in a side, cross-sectional view, a distal portion of an embodiment of the disclosed endoscope device with another embodiment of a distal tip portion.

FIG. 10 is a diagram of the insertion end 144 showing variations of the distal tip portion 402, in which, similar to FIG. 8, unbalance exists in the space between the inner peripheral surface of the elongate internal channel 206, and the outer peripheral surface of the connecting portion extends radially outward and axially forward relative to the axis of the procedure tube 208, forward viewed from the distal end 412 of the procedure tube 208 (for illustration purposes, this direction is shown by arrow D2). This configuration allows larger fragments of the urinary stones and the like to go through the elongate internal channel 206 due to the unbalance in space 446, as well as reducing the need for the operator to move the procedure tube 208 to further protrude out from the elongate internal channel 206 in order for the larger fragments to go through the space between the inner peripheral surface of the elongate internal channel 206 and the outer peripheral surface of the procedure tube 208.

Figure 11A:
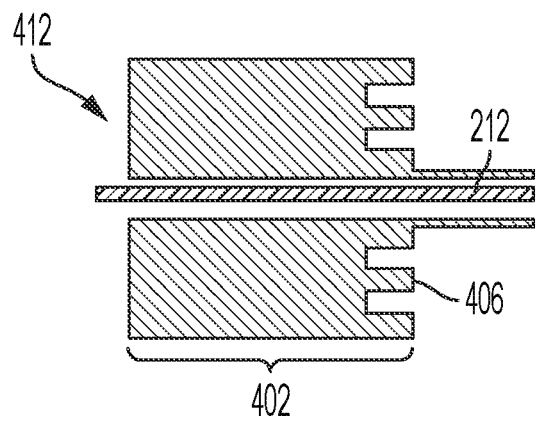
FIGS. 11A and B schematically illustrates, in a side, cross-sectional view, a distal portion of an embodiment of the disclosed endoscope device with another embodiment of a distal tip portion.
Figure 11B:
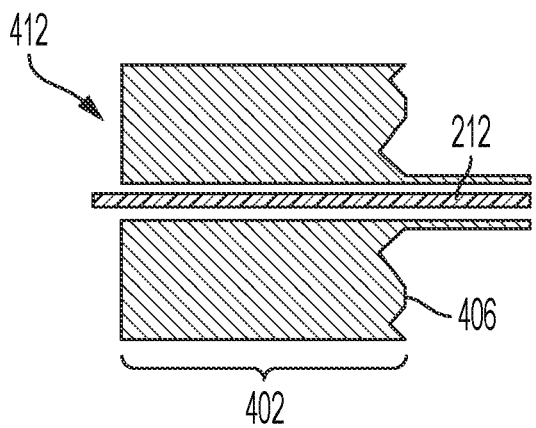

FIG. 11A is a diagram showing one embodiment of the outer peripheral surface of the connecting portion 406 being regularly serrated. In the illustrated embodiment, the regular serration is crenellated. Other regular serrations can be used, such as saw tooth. The regularly serrated outer peripheral surface of the connecting portion 406 serves to capture the fragments of urinary stones up to a certain size and the like between its serration and carry it out when the procedure tube 208 is retracted. FIG. 11B shows a diagram showing the outer peripheral surface of the connecting portion 406 being or irregularly serrated. The irregularly serrated outer peripheral surface of the connecting portion 406 also serves to capture different sizes of fragments of urinary stones and carry it out through the elongate internal channel 206. The irregularity of the serration may be optimized in accordance with the procedure the operator and the types of objects to be carried out from the patient.

Figure 12:
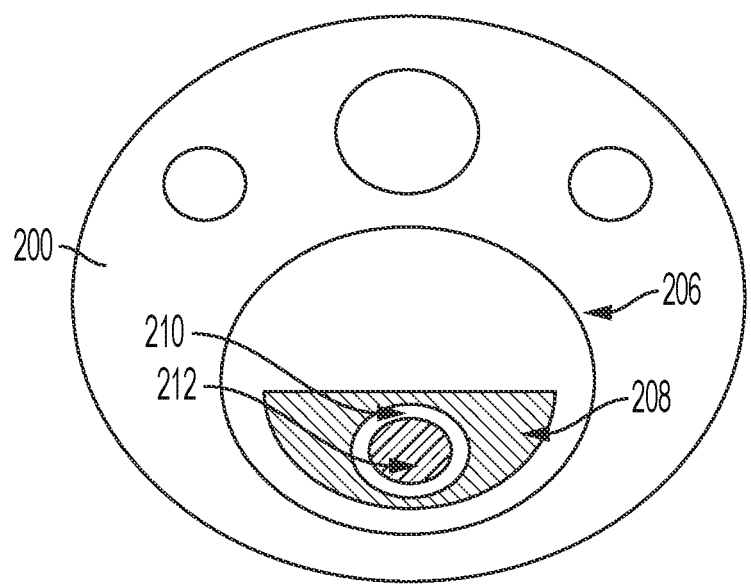
FIG. 12 schematically illustrates, in an end view, a distal portion of the embodiment of the disclosed endoscope.

FIG. 12 is a diagram of the insertion end 144 showing another variation of the distal tip portion 402. The distal end portion 402 of the procedure tube 208 is configured to cover about half of the elongate internal channel 206, and the tip of the distal tip portion 402 is configured to be semi-circular shape. This configuration of the distal end portion 402 allows large fragments of crushed urinary stones to be suctioned and pass through the elongate internal channel 206 without being blocked by the distal end portion 402. The semi-circular shape of the procedure tube 208 allows the procedure tube 208 to be inserted into and positioned within the elongate internal channel 206 at or within a predetermined position.

Figure 13:
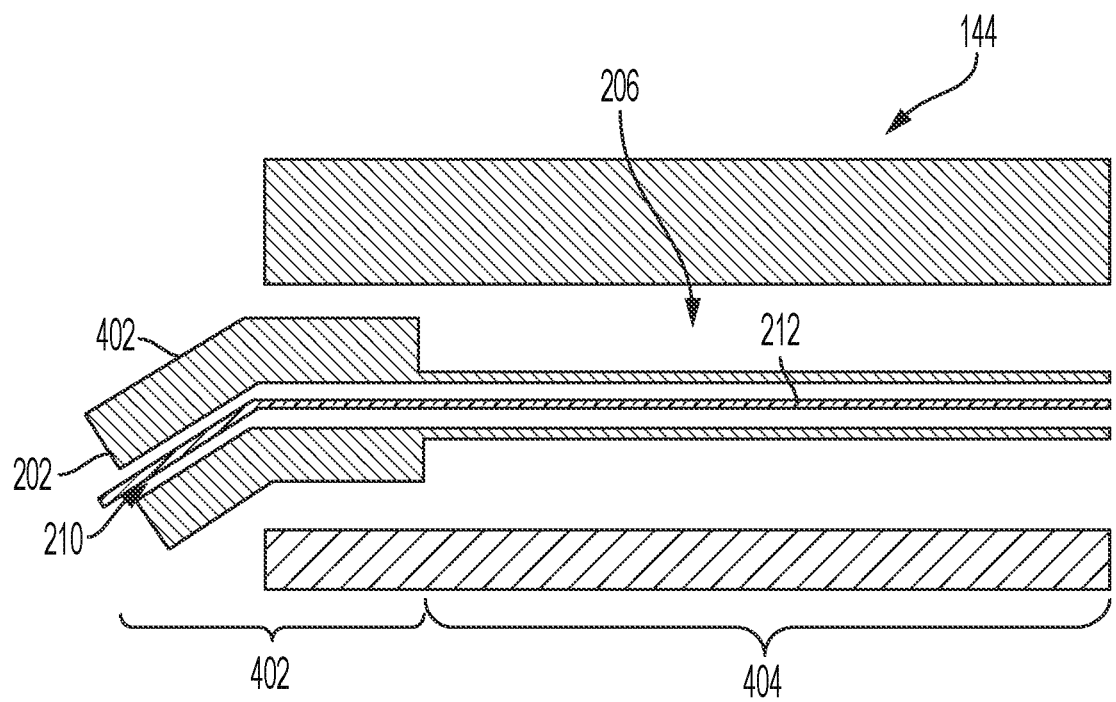
FIG. 13 schematically illustrates, in a side, cross-sectional view, a distal portion of an embodiment of the disclosed endoscope device with another embodiment of a distal tip portion.
Figure 14:
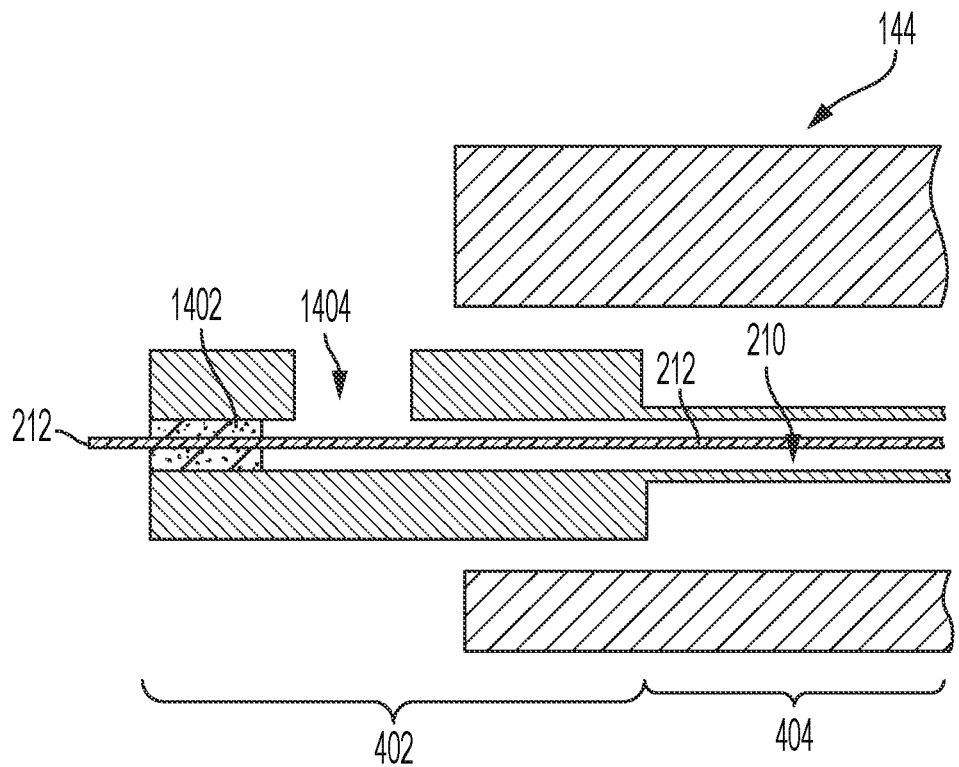
FIG. 14 schematically illustrates, in a side, cross-sectional view, a distal portion of an embodiment of the disclosed endoscope device with another embodiment of a distal tip portion.

FIG. 13 is a diagram of the insertion end 144 showing another variation of the distal tip portion 402. In the illustrated embodiment, the distal tip portion 402 includes a flexible section capable of manipulation by an operator. The distal tip portion 402 includes a plurality of bending pieces and each piece is bendable in a predetermined direction deflectable at an angle relative to a central axis of the distal tip portion, allowing the operator to direct the observation window 202 or the water supply channel 210 in a desirable direction. For example, a distal end of the bending wire can be fixed to the distal bending piece, and a proximal end of the bending wire can be connected to the bending knob placed at the operation end of the elongate internal channel 206, which allows the operator to operate the bending knob at control section 132 to bend the flexible portion. In example embodiments, the flexible portion of the distal tip portion 402 is configured by laminating a flex, a blade, and an outer coat resin and the flex is a flexible member consisting of a flat plate material spirally wound to consist a spiral tube. The blade is a metal mesh tube formed on the outer peripheral portion of the flex. The outer coat resin is formed on the outer peripheral portion of the blade, the resin material inserted between the metal element wires of the blade. Therefore, the flexible portion of the distal tip portion 402 has a certain degree of rigidity and flexibility. FIG. 14 is a diagram of the insertion end 144 showing another variation of the distal tip portion 402. In the illustrated embodiment, the laser fiber 212 extendible along the water supply channel 210 is affixed to the distal tip portion 402 of the procedure tube 208 through fixing material 1402. Example fixing materials include elastomer with a slit. In this case, a water opening 1404 would be separately placed at the sidewall of the distal tip portion 402 to prevent the target aimed at laser fiber 212 from being blown away by the fluid gushing out from the water opening. One way to suction larger fragments through the elongate internal channel 206 is to reduce the overall diameter of the procedure tube 208. In the current embodiment, the overall diameter of the procedure tube 208 is reduced, which would also reduce the diameter of the water supply channel 210, leading to an increased flow velocity of the water supplied to the crushed fragments, risking the fragments to be blown away. However, in the current embodiment, because the direction of the water supply is aimed at a different direction as compared to the direction of the laser fiber 212 and the size of the opening may be increased to reduce the flow velocity of the water supplied to the crushed fragments regardless of the diameter of the water supply channel 210, the risk of the crushed fragments to be blown away from the procedure tube 208 is minimized.

Figure 15:
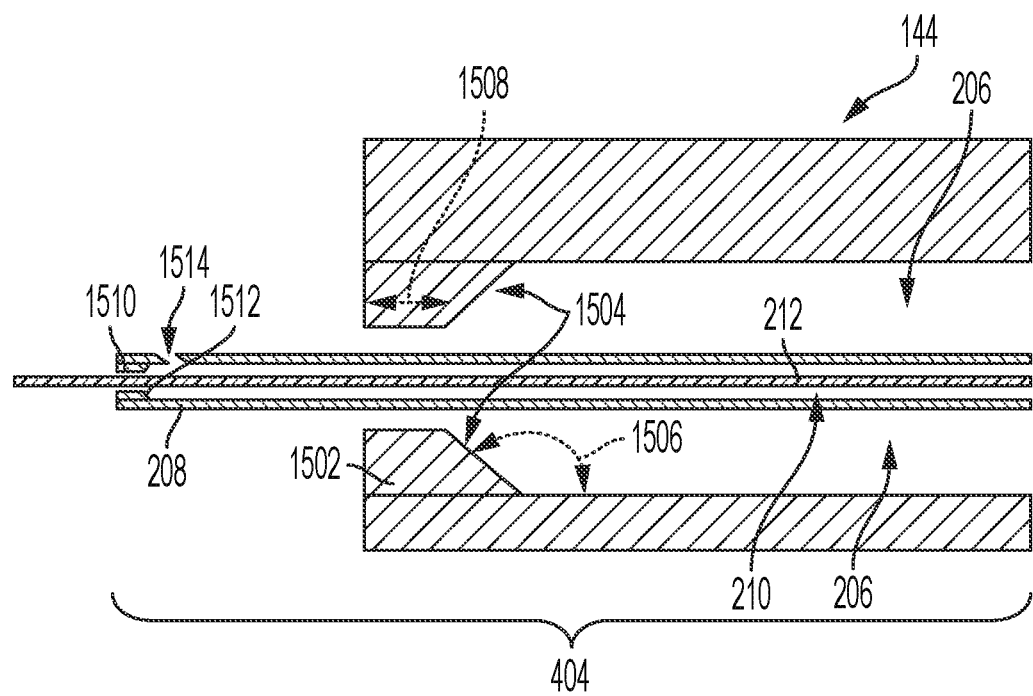
FIG. 15 schematically illustrates, in a side, cross-sectional view, a distal portion of an embodiment of the disclosed endoscope device with another embodiment of a distal tip portion.

FIG. 15 is a diagram of the insertion end 144 showing a variation of the elongate internal channel 206. In the illustrated embodiment, an inner diameter surface of the elongate internal channel 206 at the insertion end 144 includes a radially inward projecting portion 1502, and a portion 1504 having an inner diameter surface of the elongate internal channel 206 continuously decreasing in the direction of the insertion end of the insertion end 144. In order for the portion 1504 to serve to prevent the procedure tube 208 inserted into the elongate internal channel 206 to be caught by the projecting portion 1502, the angle 1506 should be more than 150 degrees. Furthermore, the longer the length 1508 is, the greater the risk of the suctioned objects to be caught between the protruding portion 1502 at the entrance of the elongate internal channel 206. By making the length 1508 smaller than the opening of the elongate internal channel 206 at the insertion end 144, the frequency of the suctioned objects to be caught between the protruding portion 1502 and the procedure tube 208 is reduced, and even if it does get caught, it would be easy to remove the caught suctioned object by retracting the procedure tube 208 from the opening of the elongate internal channel 206.

FIG. 15 also discloses another variation of the of the procedure tube 208 at the insertion end 144. In the illustrated embodiment, an inner diameter surface of the water supply channel 210 of the procedure tube 208 includes a radially inward projecting portion 1510, and a portion 1512 having an inner diameter surface of the elongate water supply channel 210 continuously decreasing in the direction of the insertion end of the procedure tube 208. With this configuration, the laser fiber 212 is less likely to be caught by the inward projecting portion 1510, making the laser fiber 212 to easily protrude from the procedure tube 208.

Even if there is a gap between the inner diameter surface of inward projecting portion 1510 and the outer diameter surface of the laser fiber 212, by making the flow path resistance of the said gap smaller than the flow path resistance of the opening 1514, a large portion of the fluid supplied through water supply/suction device 110 is discharged from water opening 1514.

By drilling the water opening 1514 obliquely to the axial direction of procedure tube 208, the direction in which the fluid is discharged from water opening 1514 becomes oblique with respect to the axial tip direction of the insertion end 144. By injecting the fluid obliquely with respect to the axial tip direction of the insertion end 144, the spiral flow reaches the crushed urinary stones and makes the collection of the urinary stones efficient.

Figure 16:
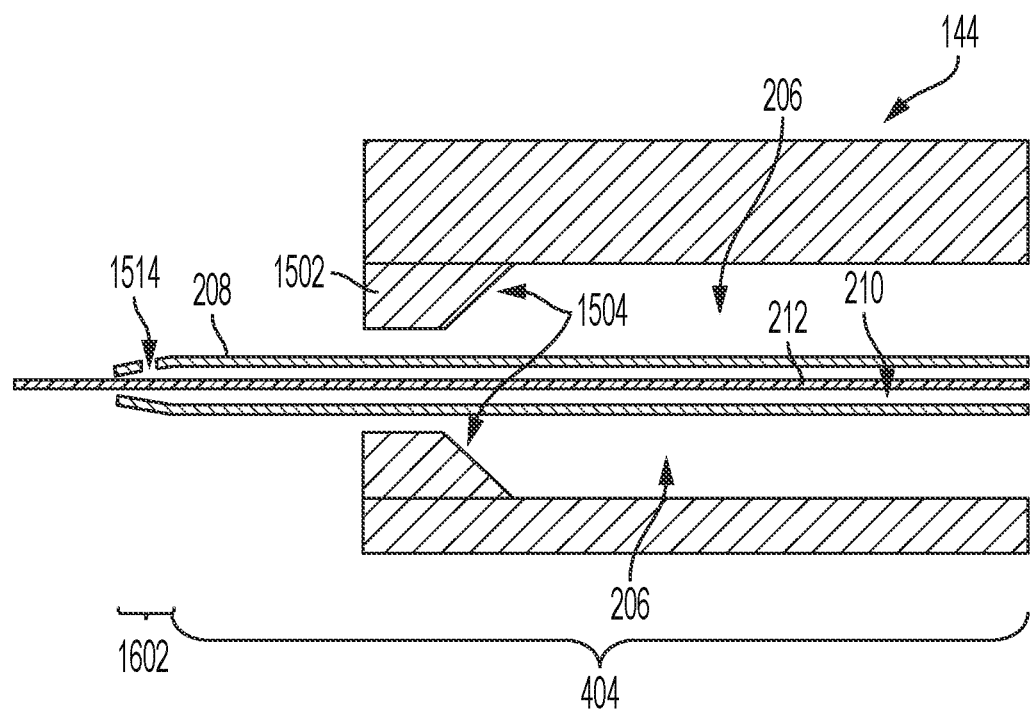
FIG. 16 schematically illustrates, in a side, cross-sectional view, a distal portion of an embodiment of the disclosed endoscope device with another embodiment of a distal tip portion.

FIG. 16 is a diagram of the insertion end 144 showing another variation of the procedure tube 208. In the illustrated embodiment, the treatment tube 208 has a continuously decreasing inner diameter and outer diameter at the distal end portion 1602. This shape prevents the laser fiber 212 from getting caught at the distal opening of the procedure tube 208 and easy to protrude out. Even if there is a gap between the tip of the inner diameter surface of the procedure tube 208 and the outer diameter surface of the laser fiber 212, by making the flow path resistance of the said gap smaller than the flow path resistance of the opening 1514, a large portion of the fluid supplied through water supply/suction device 110 is discharged from water opening 1514. In this case, the water opening 1514 is located on the side wall of the distal end 1602 to prevent the target aimed at laser fiber 212 from being blown away by the discharged fluid from the water opening 1514.

By locating water opening 1514 at the distal end 1602, the direction in which the liquid is discharged from water opening 1514 becomes substantially perpendicular to the side surface of distal end 1602, and therefore the angle becomes oblique with respect to the axial tip direction of distal end 144. By discharging the fluid obliquely with respect to the axial tip direction of the distal end 144, the spiral flow reaches the crushed urinary stones and makes the collection of the urinary stones efficient.

Figure 17:
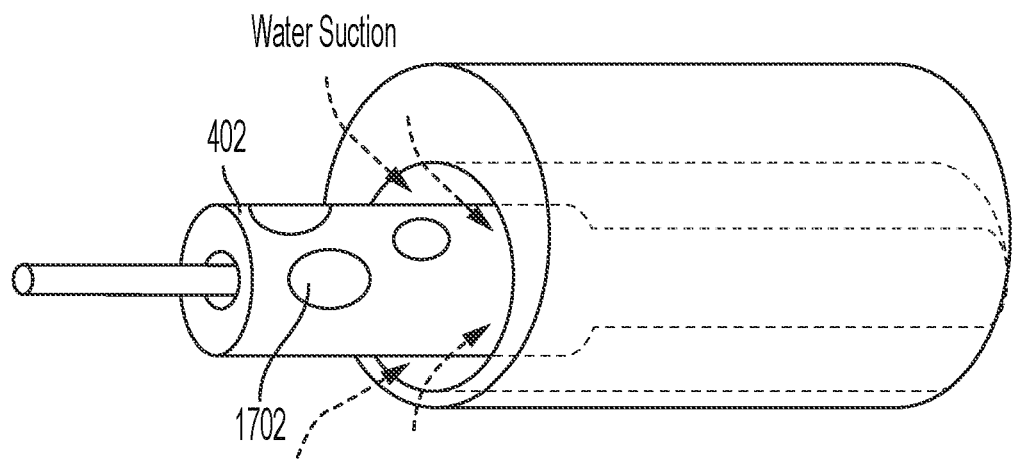
FIG. 17 schematically illustrates, in a perspective view, a distal portion of another embodiment of the disclosed endoscope device and illustrating the irrigation flow path when the features are in the illustrated positions.

FIG. 17 is a diagram of the insertion end 144 showing a variation of the distal tip portion 402. In the illustrated embodiment, the distal tip portion 402 includes openings 1702 in a wall of the procedure tube 208 that extends from the outer peripheral surface to the lumen. By providing multiple openings 1702 throughout the distal tip portion 402 and other portions of the procedure tube 208, the openings 1702 can be reduced in size without increasing the flow velocity under the same flow rate, leading to maintaining the strength of the distal tip portion 402 and preventing the laser fiber 212 from protruding out from the opening 1702.

Figure 18:
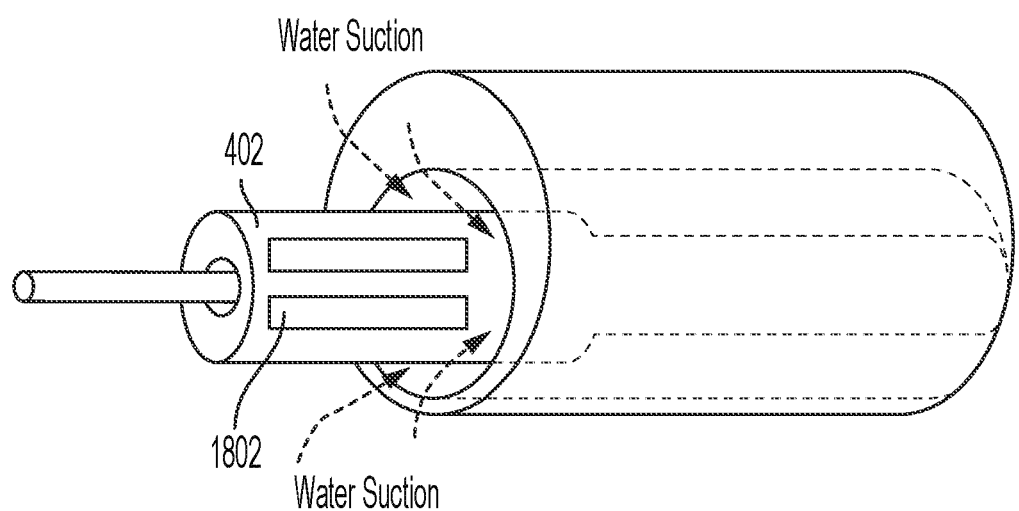
FIG. 18 schematically illustrates, in a perspective view, a distal portion of an embodiment of the disclosed endoscope device with another embodiment of a distal tip portion and illustrating the irrigation flow path when the features are in the illustrated positions FIG. 19 schematically illustrates, in a perspective view, a distal portion of an embodiment of the disclosed endoscope device with another embodiment of a distal tip portion and illustrating the irrigation flow path when the features are in the illustrated positions FIG. 20 schematically illustrates, in a perspective view, a distal portion of an embodiment of the disclosed endoscope device with another embodiment of a distal tip portion and illustrating the irrigation flow path when the features are in the illustrated positions

FIG. 18 is a diagram of the insertion end 144 showing a variation of the distal tip portion 402. In the illustrated embodiment, the distal tip portion 402 includes openings 1802 in a wall of the procedure tube 208 in a shape of a slits. The slit opening 1802 configured on the wall of the distal tip portion 402 may be a single slit, which allows the water supply through higher water pressure in order to flush the fragments of the urinary stones and the like.

Figure 19:
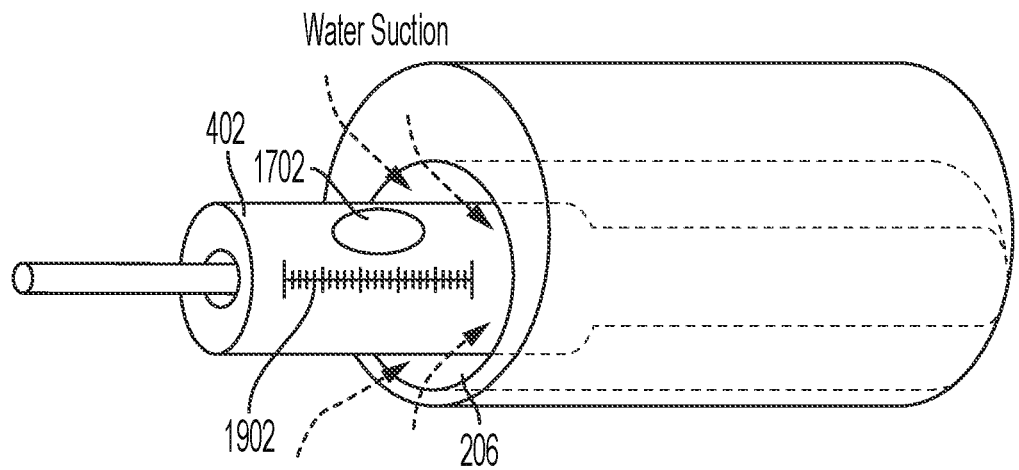

FIG. 19 is a diagram of the insertion end 144 showing a variation of the distal tip portion 402. In the illustrated embodiment, the outer peripheral surface of the distal tip portion 402 includes a measuring scale 1902. The measuring scale allows the operator to view, through another set of endoscope device, the extent the distal tip portion 402 has protruded out from the elongate internal channel 206 and the relative position of the distal tip portion 402 in relation to the elongate internal channel 206. In case the protrusion of the distal tip portion 402 is insufficient and the water opening 1702 on the side is placed within the elongate internal channel 206, the water discharged from the water opening 1702 will not flow into the patient's body and will be suctioned through the elongate internal channel 206 without exiting the endoscope device. This embodiment aims to avoid that through the measuring scale 1902. Depending on the type of endoscope with which the procedure tube 208 is combined, the amount of protrusion required for the distal tip portion 402 will vary due to differences in angle of view and the distance between the objective lens and the water supply channel 210. Therefore, the optimal allocation and configuration of the measuring scale 1902 may depend on the type of endoscope the measuring scale would be attached to. A similar measuring scale may be placed at the proximal end of the procedure tube 208 (not shown), indicating to the operator the relative position of the procedure tube 208 in relation to the operation end of the elongate internal channel 206.

Figure 20:
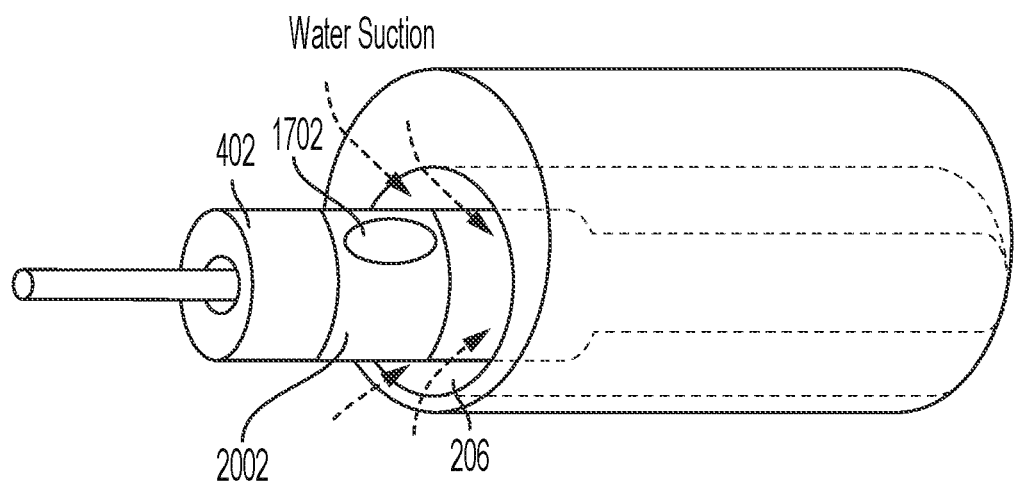
Figure 21:
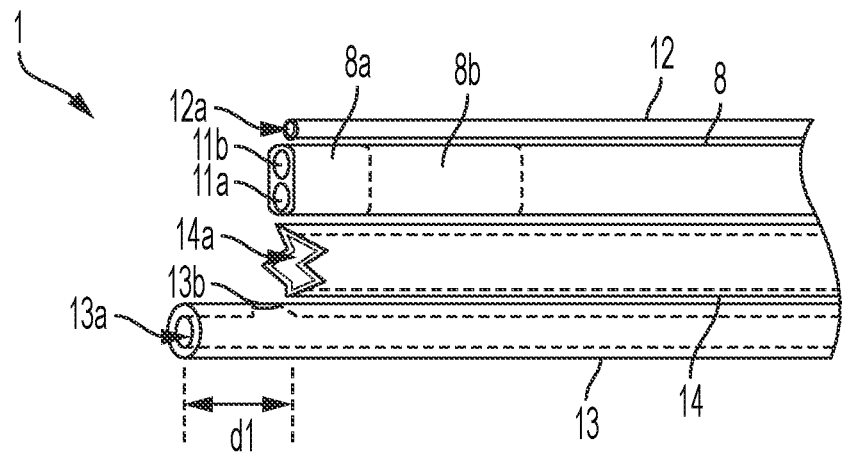
FIG. 21 is a figure of an endoscope device disclosed in the related art.
Figure 22:
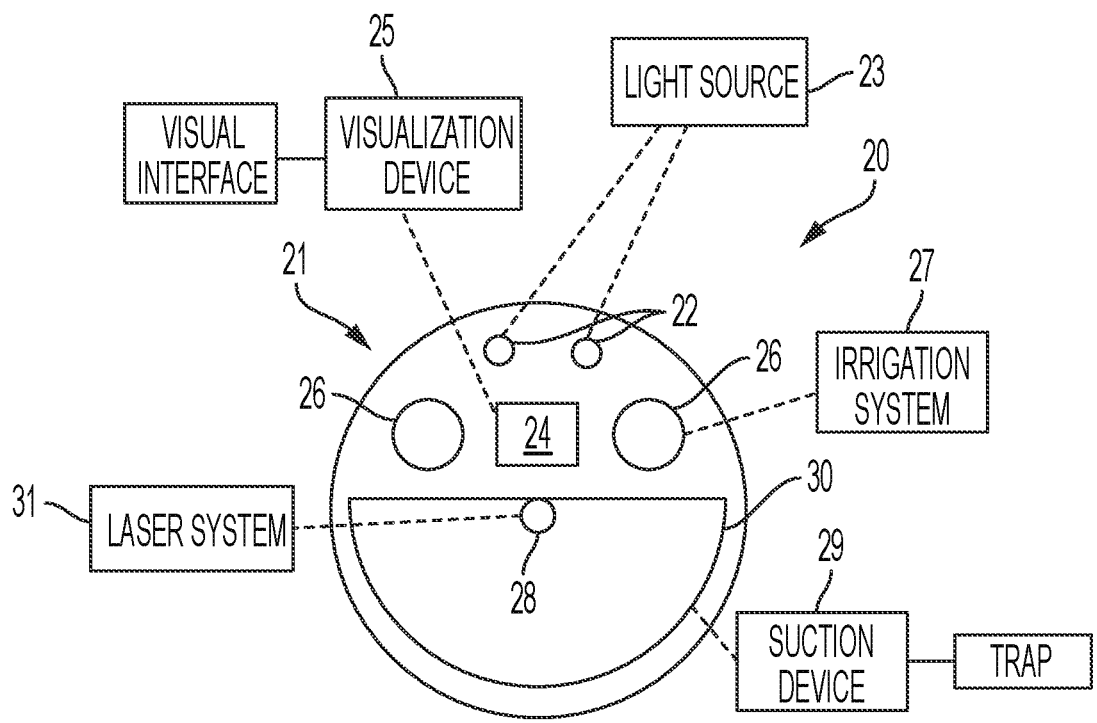
FIG. 22 illustrates an input device used in an ultrasonic observation device in the related art.

FIG. 20 is a diagram of the insertion end 144 showing a variation of the distal tip portion 402. In the illustrated embodiment, the outer peripheral surface of the distal tip portion 402 includes a different colored portion 2002 having different color compared to the other portion of the procedure tube 208. The different colored portion 2002 circumvents the distal tip portion 402 of the procedure tube 208. Through observation through the endoscope, the operator may determine the extent of the protrusion of the distal tip portion 402 of the procedure tube through observing the different colored portion 2002. By locating the water opening 1702 relative to the different colored portion 2002, the distal tip portion 402 of the procedure tube 208 may inform the operator the relevant position of the water opening 1702, providing similar effect as the measuring scale 1902 in FIG. 19. The different colored portion 2002 may be more visible compared to the than the measuring scale 1902 in case distinct coloring is used.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A medical device, comprising:
    an insertion tube having an outer tube surface and an inner tube surface; and
    a procedure tube movably disposed inside the insertion tube,
    wherein the procedure tube includes a distal tip portion and an elongate portion located proximally relative to the distal tip portion,
    wherein the distal tip portion has a distal end surface, a proximal end surface, and a circumferential side surface connecting the distal end surface to the proximal end surface,
    wherein the proximal end surface of the distal tip portion is serrated,
    wherein an outer diameter of the circumferential side surface is a first diameter, an outer diameter of the elongate portion is a second diameter, and the first diameter is larger than the second diameter,
    wherein, when the distal tip portion of the procedure tube is positioned within the insertion tube, and
    wherein a first distance is less than a second distance, where the first distance is between the inner tube surface of the insertion tube and the circumferential side surface of the distal tip portion of the procedure tube and the second distance is between the inner tube surface of the insertion tube and an outer peripheral surface of the elongate portion of the procedure tube.

2. The medical device according to claim 1, wherein the inner tube surface includes:
    an insertion end portion corresponding to a first length of the inner tube surface, and
    an axially extending portion corresponding to a second length of the inner tube surface,
    wherein the insertion end portion is located distally relative to the axially extending portion,
    wherein the insertion end portion has a first inner diameter and the axially extending portion has a second inner diameter, and
    wherein the second inner diameter is larger than the first inner diameter.

3. The medical device according claim 2, wherein the inner tube surface includes a intermediate portion, the intermediate portion connecting the insertion end portion to the axially extending portion,
    wherein an interior angle is formed between a surface of the intermediate portion and a surface of the insertion end portion, the interior angle greater than 90 degrees and less than 180 degrees, and
    wherein an exterior angle is formed between the surface of the intermediate portion and a surface of the axially extending portion, the exterior angle greater than 90 degrees and less than 180 degrees.

4. The medical device according to claim 2, further comprising a laser fiber configured to extend along a lumen of the procedure tube.

5. The medical device according to claim 2, wherein the procedure tube includes an opening in fluid communication with a lumen of the procedure tube, the opening and the lumen configured to supply fluid towards a distal end of the procedure tube.

6. The medical device according to claim 5, wherein the opening is a slit.

7. The medical device according to claim 5, wherein a central axis of the opening is oblique relative to a longitudinal axial of the procedure tube.

8. A medical device, comprising:
    a procedure tube configured to move in an insertion tube, wherein the procedure tube includes:
    a distal tip portion, and
    an elongate portion located proximally relative to the distal tip portion,
    wherein the distal tip portion has a distal end surface, a proximal end surface, and a circumferential side surface connecting the distal end surface to the proximal end surface,
    wherein the proximal end surface of the distal tip portion is serrated,
    wherein the circumferential side surface of the distal tip portion has a first diameter and an outer peripheral surface of the elongate portion has a second diameter, and
    wherein the first diameter is larger than the second diameter.

9. The medical device according to claim 8, wherein an inner tube surface of the procedure tube includes a intermediate portion, the intermediate portion connecting the distal tip portion to the elongate portion,
    wherein an interior angle is formed between a surface of the intermediate portion and the circumferential side surface of the distal tip portion, the interior angle greater than 90 degrees and less than 180 degrees, and
    wherein an exterior angle is formed between the surface of the intermediate portion and the outer peripheral surface of the elongate portion, the exterior angle greater than 90 degrees and less than 180 degrees.

10. The medical device according to claim 8, further comprising a laser fiber configured to extend along a lumen of the procedure tube.

11. The medical device according to claim 8, wherein the procedure tube includes an opening in fluid communication with a lumen of the procedure tube, the opening and the lumen configured to supply fluid towards a distal end of the procedure tube.

12. The medical device according to claim 11, wherein the opening is a slit.

13. The medical device according to claim 11, wherein the central axis of the opening is oblique relative to the longitudinal axial of the procedure tube.

14. The medical device according to claim 8, wherein the circumferential side surface of the distal tip portion of the procedure tube includes a plurality of openings, each of the plurality of openings extending from a first end in the circumferential side surface to a second end in an inner diameter surface of the procedure tube, and wherein the plurality of openings are configured to supply a fluid to the first end of each of the plurality of openings.

15. The medical device according to claim 8, wherein the proximal end surface of the distal tip portion is inclined to face toward the outer peripheral surface of the elongate portion.

16. The medical device according to claim 8, wherein the proximal end surface of the distal tip portion is regularly serrated.

17. The medical device according to claim 8, wherein the proximal end surface of the distal tip portion is irregularly serrated.

18. The medical device according to claim 8, further comprising an operation wire,
wherein the distal tip portion is configured to bend, and
wherein the operation wire is attached to the distal tip portion and is configured to bend the distal tip portion in a predetermined direction deflectable at an angle relative to a central axis of the distal tip portion.

\* \* \* \* \*